United States Patent [19]

Mertens et al.

[11] Patent Number: 4,695,567
[45] Date of Patent: Sep. 22, 1987

[54] PYRROLOBENZIMIDAZOLES, PHARMACEUTICAL COMPOSITIONS CONTAINING THEM AND METHOD OF USING THEM TO TREAT CERTAIN HEART AND CIRCULATORY DISEASES

[75] Inventors: Alfred Mertens, Schriesheim; Jens-Peter Hölck; Herbert Berger, both of Mannheim; Bernd Müller-Beckmann, Grünstadt; Klaus Strein, Hemsbach; Egon Roesch, Mannheim, all of Fed. Rep. of Germany

[73] Assignee: Boehringer Mannheim GmbH, Mannheim, Fed. Rep. of Germany

[21] Appl. No.: 820,259

[22] Filed: Jan. 17, 1986

[30] Foreign Application Priority Data

Jan. 18, 1985 [DE] Fed. Rep. of Germany ....... 3501497

[51] Int. Cl.$^4$ .................. A61K 31/50; A61K 31/505; C07D 403/06; C07D 487/04
[52] U.S. Cl. .................................. 514/253; 514/254; 514/256; 514/269; 514/272; 514/274; 514/275; 514/359; 514/361; 514/362; 514/363; 514/364; 514/365; 514/369; 514/370; 514/372; 514/376; 514/377; 514/378; 514/380; 514/383; 514/394; 544/238; 544/298; 544/300; 544/310; 544/316; 544/317; 544/319; 544/320; 544/321; 544/328; 544/331; 544/333; 544/405; 548/125; 548/127; 548/128; 548/129; 548/130; 548/131; 548/132; 548/133; 548/134; 548/135; 548/136; 548/137; 548/138; 548/141; 548/142; 548/143; 548/144; 548/181; 548/206; 548/213; 548/214; 548/226; 548/227; 548/228; 548/229; 548/230; 548/231; 548/232; 548/233; 548/235; 548/236; 548/240; 548/243; 548/244; 548/245; 548/246; 548/247; 548/248; 548/249; 548/255; 548/262; 548/263; 548/264; 548/266; 548/267; 548/269; 548/326
[58] Field of Search ............... 544/294, 300, 310, 316, 544/317, 319, 320, 321, 298, 324, 328, 331, 333, 238, 405; 548/181, 213, 214, 326, 125, 127, 128, 129, 130, 131, 132, 133, 134, 135, 136, 137, 138, 141, 142, 43, 144, 206, 226, 227, 228, 229, 230, 231, 232, 233, 235, 236, 240, 243, 244, 245, 246, 247, 248, 249, 258, 262, 263, 266, 267, 269; 514/253, 269, 272, 274, 275, 256, 369, 370, 372, 394, 254, 359, 361, 362, 363, 364, 365, 376, 377, 378, 380, 383

[56] References Cited

U.S. PATENT DOCUMENTS 4,327,099  4/1982  Evans et al. ................... 548/326
4,548,946  10/1985  Finizio ........................... 514/338
4,552,876  11/1985  Jones et al. .................... 514/338
4,563,455  1/1986  Ueda et al. ..................... 514/338

FOREIGN PATENT DOCUMENTS 45200  2/1982  European Pat. Off. ............ 514/338
161632  11/1985  European Pat. Off. ............ 514/338
2004281  3/1979  United Kingdom ............... 514/338

OTHER PUBLICATIONS

Burger, *Medicinal Chemistry*, 2nd Edit., pp. 565–571, 579–581, and 599–602 (1960).
Remington's *Pharmaceutical Sciences*, 14th Ed., 1970, pp. 528–529.

Primary Examiner—Henry R. Jiles
Assistant Examiner—Kurt G. Briscoe
Attorney, Agent, or Firm—Felfe & Lynch

[57] ABSTRACT

The present invention provided pyrrolobenzimidazoles or tautomer thereof, of the general formula:

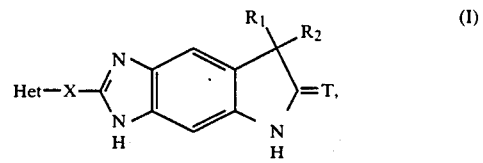

wherein
$R_1$ is hydrogen, $C_1$–$C_6$ alkyl, $C_2$–$C_6$ alkenyl or $C_3$–$C_7$ cycloalkyl;
$R_2$ is hydrogen, cyano, $C_1$–$C_6$ alkyl, $C_2$–$C_6$ alkenyl, or a carbonyl group substituted by hydroxyl, $C_1$–$C_6$ alkyl, $C_1$–$C_6$ alkyoxy, amino, $C_1$–$C_6$ alkylamino, $C_2$–$C_{12}$ dialkylamino or hydrazino, or
$R_2$ and $R_1$ together with the carbon to which they are attached form a $C_3$–$C_8$ spirocycloalkyl ring, or $R_1$ and $R_2$ together form $C_3$–$C_7$ alkylidene or $C_3$–$C_7$ cycloalkylkidene,
X is a valency bond, $C_1$–$C_4$ alkylene or vinylene and
T is oxygen or sulphur;
and Het is furanyl, thienyl, pyrrolyl, pyrazolyl, imidazolyl, oxazolyl, thiazolyl, triazolyl, oxadiazolyl, thiadiazolyl, pyrazinyl, pyrimidinyl or pyridazinyl wherein the heterocyclic five- and six-membered rings are unsubstituted or substituted by one or more $C_1$–$C_6$ alkyl, $C_1$–$C_6$ alkoxy, $C_1$–$C_6$ alkylthio, hydroxyl, oxo, nitro, amino, halo, carboxyl, $C_2$–$C_7$ alkoxycarbonyl, aminocarbonyl or cyano groups; or a physiologically acceptable salt thereof with an inorganic or organic acid. These compounds are useful for treating heart or circulatory diseases, especially those which respond to a change of blood pressure, an increase in cardiac output and/or a change in micro-circulation.

18 Claims, No Drawings

PYRROLOBENZIMIDAZOLES, PHARMACEUTICAL COMPOSITIONS CONTAINING THEM AND METHOD OF USING THEM TO TREAT CERTAIN HEART AND CIRCULATORY DISEASES

The present invention is concerned with new pyrrolobenzimidazoles, processes for the preparation thereof and pharmaceutical compositions containing them, as well as with intermediates for the preparation thereof.

The new pyrrolobenzimidazoles according to the present invention are compounds of the general formula:

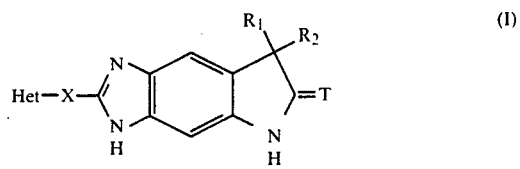

wherein $R_1$ is a hydrogen atom or an alkyl, alkenyl or cycloalkyl radical, $R_2$ is a hydrogen atom, an alkyl or alkenyl radical, a cyano group, a carbonyl group substituted by a hydroxyl, alkyl, alkoxy, amino, alkylamino, dialkylamino or hydrazino group or, together with $R_1$, represents a cycloalkylene radical or $R_1$ and $R_2$ together form an alkylidene or cycloalkylidene radical, X is a valency bond, a $C_1$–$C_4$ alkylene radical or a vinylene radical, T is an oxygen or sulphur atom and Het is a heterocyclic six-membered ring with an oxygen or sulphur atom, a heterocyclic five-membered ring with 1 to 4 heteroatoms or a heterocyclic six-membered ring with 2 to 5 heteroatoms, whereby the hetero atoms of the said five- or six-membered rings can be the same or different and are nitrogen, oxygen or sulphur atoms and can optionally carry an oxygen atom on one or more nitrogen atoms and the said five- and six-membered rings can optionally be substituted by one or more alkyl, alkoxy, alkylthio, hydroxyl, oxo, nitro, amino, halogeno, carboxyl, alkoxycarbonyl, aminocarbonyl or cyano groups; their tautomers and their physiologically acceptable salts with inorganic and organic acids.

Also contemplated are compounds of formula (I) wherein $R_1$ is hydrogen, methyl, ethyl, cyclopentyl or cyclohexyl, and $R_2$ is hydrogen, methyl, ethyl, isopropyl, 3-pentyl, allyl, cyano, acetyl, propionyl, methoxycarbonyl, ethoxycarbonyl, aminocarbonyl, methylaminocarbonyl, dimethylaminocarbonyl or hydrazinocarbonyl or $R_1$ and $R_2$, together with the carbon atom to which they are attached, represent a spirocyclopropyl, spirocyclobutyl, spirocyclopentyl or spirocyclohexyl ring or $R_1$ and $R_2$ together represent isopropylidene, X is a valency bond, or methylene or vinylene, T is oxygen and Het is a pyrrolyl, furanyl, thiophenyl, pyrazolyl, imidazolyl, thiazolyl, oxazolyl, triazolyl, tetrazolyl, thiadiazolyl, pyronyl, oxadizolyl, pyrazinyl, N,N-dioxypyrazinyl, pyrimidinyl, N,N-dioxypyrimidinyl, pyrimidinonyl, pyridazinyl, oxazinyl, thiazinyl, triazinyl or tetrazinyl, and wherein the heteroyclic five- or six-membered rings can be substituted one or more times by oxo, hydroxyl, methyl, methoxy, methylthio, carboxyl, methoxycarbonyl, ethoxycarbonyl, aminocarbonyl, amino, nitro, halo or cyano.

Since the compounds of general formula (I), when $R_1$ is not the same as $R_2$, possess an asymmetric carbon atom, the present invention also includes the optically-active forms and the racemic mixtures of these compounds.

The new compounds according to the present invention possess valuable pharmacological properties and, in particular, they increase the strength of the heart and/or have a blood pressure-lowering action and/or influence the thrombocyte function and improve the microcirculation.

In general formula (I), the substituents $R_1$ and/or $R_2$ preferably represent hydrogen atoms, straight-chained or branched alkyl or alkylene radicals containing 1 to 6 and 2 to 6 carbon atoms, respectively, cycloalkyl radicals containing 3 to 7 carbon atoms, cyano groups or carboxyl groups substituted by a hydroxyl, alkyl, alkoxy, amino, alkylamino, dialkylamino or hydrazino group, wherein the alkyl moiety contains up to 6 and preferably up to 3 carbon atoms. More particularly, $R_1$ and/or $R_2$ can represent hydrogen atoms, methyl, ethyl, isopropyl, 3-pentyl, cyclopentyl, cyclohexyl, allyl, cyano, acetyl, propionyl, methoxycarbonyl, ethoxycarbonyl, aminocarbonyl, methylaminocarbonyl, dimethylaminocarbonyl or hydrazinocarbonyl groups.

$R_1$ and $R_2$ can, together with the carbon atom to which they are attached, also form a cycloalkyl ring containing 3 to 8 carbon atoms and preferably a spirocyclopropyl, spirocyclobutyl, spirocyclopentyl or spirocyclohexyl radical.

$R_1$ and $R_2$ can together also form an alkylidene or cycloalkylidene radical and preferably an isopropylidene radical.

X is a valency bond, a $C_1$–$C_4$ alkylene radical or a vinylene radical but preferably a valency bond or a methylene or vinylene radical.

T is an oxygen or sulphur atom but preferably an oxygen atom.

If Het signifies a heterocyclic six-membered ring with one oxygen or one sulphur atom, a heterocyclic five-membered ring with 1 to 4 heteroatoms or a heterocyclic six-membered ring with 2 to 5 heteroatoms, wherein the heteroatoms of the said five- and six-membered rings can be the same or different and signify nitrogen, oxygen or sulphur and can possibly carry an oxygen atom on one or more nitrogen atoms, pyrrolyl, furanyl, thiophenyl, pyrazolyl, imidazolyl, thiazolyl, oxazolyl, pyronyl, triazolyl, tetrazolyl, thiadiazolyl, oxadiazolyl, pyrazinyl, N,N-dioxypyrazinyl, pyrimidinyl, N,N-dioxypyrimidinyl, pyridazinyl, oxazinyl, thiazinyl, triazinyl or tetrazinyl.

Alkyl, alkoxy and alkylthio substituents in the heterocyclic five- and six-membered rings can contain up to 6 and preferably up to 4 carbon atoms, the methyl, ethyl, methoxy, ethoxy, methylthio and ethylthio radicals being preferred.

Halogen is to be understood to mean fluorine, chlorine or bromine, chlorine being preferred.

Preferred substituents of the heterocyclic five-and six-membered rings include oxo, hydroxyl, methyl, methoxy, methylthio, carboxyl, methoxycarbonyl, ethoxycarbonyl, aminocarbonyl, amino, nitro, halogeno or cyano groups and especially hydroxyl, methyl, methylthio, carboxyl, methoxycarbonyl, aminocarbonyl and cyano groups. The oxo-substituted heterocyclic five- or six-membered rings can carry an oxygen atom on the carbon atom of the ring and can be for example pyrone or pyrimidinone.

The compounds of general formula (I) can be prepared according to the following reaction schemes 1 and 2.

As can be seen from scheme 1, compounds of general formulae (II) and (III) are converted by nitration or by acylation of the aminonitroindolinones (IV) and (V) with compounds of general formula (IX) into compounds of general formulae (VI) and (VII), wherein $R_1$, $R_2$, Het and X have the same meanings as above. From compounds of general formulae (VI) and (VII), by reduction of the nitro group, or from compounds of general formula (VIII) by reaction with compounds of general formula (IX), there are obtained compounds of general formula (I) or tautomers thereof, wherein $R_1$, $R_2$, Het and X have the same meanings as above.

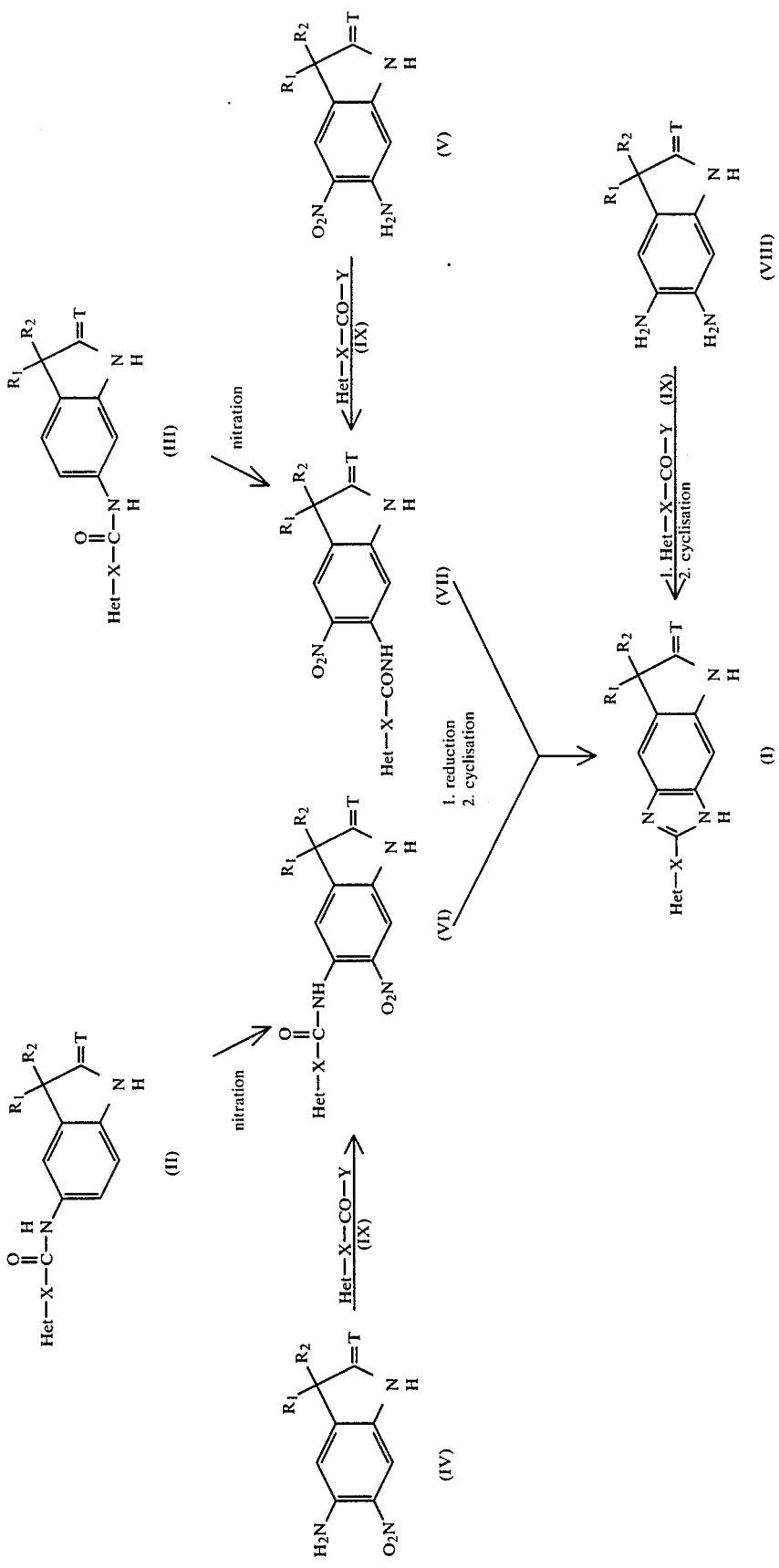
scheme 1

In general formula (IX), Het and X have the above-given meanings and Y is either a hydrogen atom or a residue which can easily be split off. In particular, compounds of general formula (IX) are to be understood to be aldehydes, as well as acid halides, such as acid chlorides, carboxylic acid esters, for example methyl and ethyl esters, and other activated carboxylic acid derivatives, for example anhydrides.

If the compound of general formula (IX) is an aldehyde, the reaction to the Schiff base with compounds of general formula (VIII) preferably takes place in an alcoholic medium, the subsequent cyclisation and oxidation to give compounds of general formula (I) taking place by heating the reaction mixture under reflux in the presence of atmospheric oxygen and catalytic amounts of an acid, for example toluene sulphonic acid.

If the compound of general formula (IX) is a carboxylic acid derivative, the reaction with a compound of general formulae (VI), (VII) and (VIII) to give an amide suitably takes place in an inert solvent, preferably in methylene chloride or pyridine, and the subsequent cyclisation to give compounds of general formula (I) is, after previous hydrogenation of the nitro group in compounds of general formulae (VI) and (VII), carried out in a solvent or solvent mixture, for example ethanol, isopropanol, glacial acetic acid, benzene, chlorobenzene, glycol, diethylene glycol dimethyl ether, sulfolan or dimethylformamide, at a temperature of from 0° to 250° C. but preferably at the boiling point of the reaction mixture, optionally in the presence of a condensation agent, for example phosphorus oxychloride, thionyl chloride, p-toluene-sulphonic acid, hydrochloric acid, sulphuric acid, phosphoric acid or polyphosphoric acid, or possibly in the presence of a base, for example sodium hydroxide, potassium methylate or potassium tert.-butylate. However, the cyclisation can also be carried out without the use of a solvent and/or of a condensation agent.

The above-mentioned hydrogenation of the nitro group is preferably carried out in a solvent, for example water, ethanol, glacial acetic acid, ethyl acetate or dimethylformamide, preferably with hydrogen in the presence of a hydrogenation catalyst, for example Raney nickel, platinum or palladium/charcoal, or with a metal, for example, iron, tin or zinc, in the presence of an acid, or with a salt, for example ferrous sulphate, stannous chloride, sodium sulphide, sodium hydrogen sulphide or sodium dithionite, or with hydrazine in the presence of Raney nickel, at a temperature of from 0° to 250° C. but preferably at ambient temperature.

The compounds of general formulae (IV), (V) and (VIII) are known from the literature (cf. Federal Republic of Germany Patent Application No. P 34 17 643.8). Compounds of general formula (VI) and (VII) are new and are also the subject of the present invention.

As can be seen from scheme 2, the compounds of general formula (I) and the tautomeric forms thereof can also be prepared by various processes known from the literature from compounds of general formula (X), wherein Het and X have the above-given meanings (cf. in this regard, R. C. Elderfield (ed.); P. L. Julian, E. W. Meyer and H. C. Printy, Heterocyclic Compounds, Vol. 3, 126-142, pub. John Wiley & Sons, 1952, New York).

Hinsberg synthesis: reaction of aromatic amines with the bisulphite addition compounds of ketones Brunner synthesis: cyclisation of aromatic amines via the hydrazite to oxindoles.

Stolle synthesis: cyclisation of aromatic amines via an amide to the oxindole.

Scheme 2

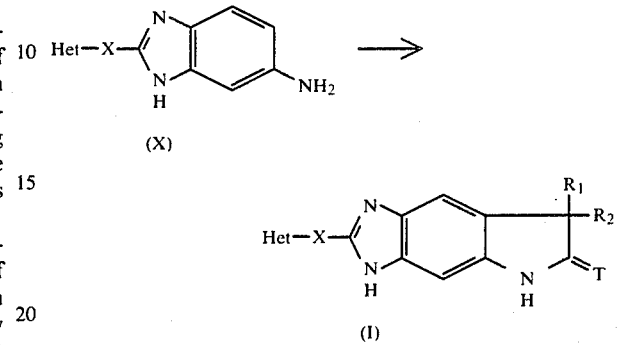

Some of the compounds of general formula (X) are new and can be prepared by processes known from the literature.

Compounds of general formula (I) can also be subsequently converted into other compounds of general formula (I). This applies, for example:

(a) For the oxidation of a five- or six-membered ring with one or more nitrogen atoms to give the corresponding N-oxides, the oxidation is preferably carried out with one or more equivalents of the oxidation agent employed, for example with hydrogen peroxide in glacial acetic acid, trifluoroacetic acid or formic acid at 20° to 100° C. or in acetone at 0° to 60° C.; with a per acid, for example performic acid or m-chloroperbenzoic acid, in glacial acetic acid, trifluoroacetic acid, methylene chloride or chloroform, at a temperature of from 0° to 60° C.

(b) For the hydrogenation of a vinylene compound (X=—CH=CH—) into the corresponding ethylene compound (X=—$CH_2$—$CH_2$—), the hydrogenation is preferably carried out in a solvent, for example water, water/ethanol, methanol, glacial acetic acid, ethyl acetate or dimethylformamide, preferably with hydrogen in the presence of a hydrogenation catalyst, for example Raney nickel, platinum or palladium/charcoal.

(c) For the reaction of a compound of general formula (I), wherein $R_1$ and $R_2$ are hydrogen atoms, with a compound of the general formula:

wherein $R_3$ and $R_4$ are alkyl radicals or $R_3$ together with $R_4$ forms a $C_3$-$C_7$-cycloalkylene radical, to give a compound of general formula (I), wherein $R_1$ together with $R_2$ represents an alkylidene or cycloalkylidene radical, as well as the optional hydrogenation thereof to give corresponding compounds of general formula (I), wherein $R_1$ and $R_2$ are hydrogen atoms.

The reaction with compounds of general formula (XI) is preferably carried out in a polar solvent, for example ethanol or dimethylformamide, in the presence of a base, for example ammonia or triethylamine, or also in the presence of an acid, for example hydrochloric acid, sulphuric acid, phosphoric acid, polyphosphoric acid or p-toluenesulphonic acid, at 20° to 250° C. but preferably at the boiling temperature of the solvent.

The hydrogenation which is optionally to be carried out is carried out under the conditions described above under (b).

(d) For the reaction of compounds of general formula (I), wherein $R_1$ or $R_2$ is a carboxyl group or a reactive derivative thereof, for example an ester or acid chloride, with hydrazine or with an amine of the general formula:

$$R_5-NH-R_6 \qquad (XII)$$

wherein $R_5$ and $R_6$, which can be the same or different, are hydrogen atoms or alkyl radicals containing up to 5 carbon atoms, or with a reactive derivative thereof, if $R_1$ or $R_2$ is a carboxyl group, to give compounds of general formula (I), wherein $R_2$ is a carboxyl group substituted by an amino, alkylamino, dialkylamino or hydrazino group.

The reaction is preferably carried out in a solvent or solvent mixture, for example methylene chloride, ethanol, chloroform, carbon tetrachloride, diethyl ether, tetrahydrofuran, dioxan, benzene, acetonitrile or dimethylformamide, optionally in the presence of an agent activating the acid or of a water-removing agent, for example in the presence of ethyl chloroformate, thionyl chloride, phosphorus trichloride, phosphorus pentoxide, N′,N-dicyclohexyl carbodiimide, N′,N-dicyclohexyl carbodiimide/N-hydroxysuccinimide, N,N′-carbonyldiimidazole or N,N′-thionyl diimidazole or of triphenyl phosphine/carbon tetrachloride, or of an agent activating the hydrazino or amino group, for example phosphorus trichloride, and optionally in the presence of an inorganic base, for example sodium carbonate, or of a tertiary organic base, for example triethylamine or pyridine; which can simultaneously serve as a solvent, at a temperature of from −25° to 250° C. but preferably at a temperature of from −10° C. and the boiling temperature of the solvent used. Furthermore, water formed during the reaction can be separated off by azeotropic distillation, for example by heating with toluene on a water separator, or by the addition of a drying agent, for example anhydrous magnesium sulphate or a molecular sieve.

However, the reaction is carried out especially advantageously in a corresponding halide, for example the carboxylic acid chloride, and hydrazine or a corresponding amine, whereby these can simultaneously serve as solvent, at a temperature of from 0° to 50° C.

(e) For the reaction of a compound of general formula (I), wherein $R_1$ or $R_2$ represents an aminocarbonyl group, to give a compound of general formula (I), wherein $R_1$ or $R_2$ is a cyano group, the reaction is preferably carried out in an inert solvent, for example methylene chloride, chloroform, dioxan, pyridine, xylene or chlorobenzene, in the presence of a water-removing agent, for example thionyl chloride, phosphorus trichloride, phosphorus pentoxide, phosphorus pentachloride, aluminium chloride, benzenesulphonic acid chloride, toluenesulphonic acid chloride, triphenyl phosphine, boron trifluoride or ethyl polyphosphate, at a temperature of from 50° to 250° C. but preferably at the boiling temperature of the solvent.

(f) For the reaction of a compound of general formula (I), wherein $R_1$ or $R_2$ is a cyano group, to give another compound of general formula (I), wherein $R_1$ or $R_2$ form a carboxyl, aminocarbonyl or alkoxycarbonyl with a total of up to 6 carbon atoms, alcoholysis and/or hydrolysis is preferably carried out in the presence of an acid, for example hydrochloric acid, sulphuric acid, phosphoric acid or trichloroacetic acid, or in the presence of a base, for example sodium hydroxide or potassium hydroxide, in an appropriate solvent, for example water, water/methanol, ethanol, water/isopropanol or water/dioxan, at a temperature of from −10° to 120° C., for example at a temperature of from ambient temperature to the boiling temperature of the reaction mixture.

(g) For the reaction of a compound of general formula (I), wherein T is an oxygen atom, to give another compound of general formula (I), wherein T is a sulphur atom, the reaction is carried out by processes known from the literature with a reagent transferring the sulphur atom, for example phosphorus pentasulphide, whereby 1 to 5 mole but preferably 1 mole of phosphorus pentasulphide is used in an appropriate solvent. As solvent, there can be used, for example, tetrahydrofuran, dioxan, benzene, toluene or pyridine, at a temperature of from 25° to 125° C. However, it is preferred to use pyridine with a reaction time of from 1 to 10 hours and preferably of 5 hours, depending upon the nature of the reaction components.

Furthermore, the compounds obtained in general formula (I) can, if desired, be subsequently converted into their physiologically acceptable acid-addition salts with inorganic and organic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid and methanesulphonic acid.

For the preparation of pharmaceutical compositions, the compounds of general formula (I) can be mixed in known manner with appropriate pharmaceutical carrier substances, aroma, flavouring and colouring materials and formed, for example, into tablets or dragees or, with the addition of appropriate adjuvants, can be suspended or dissolved in water or an oil, for example olive oil.

The new compounds of general formula (I) according to the present invention and the salts thereof can be administered enterally or parenterally in liquid or solid form. As injection medium, it is preferred to use water which contains the additives usual for injection solutions, for example stabilising agents, solubilising agents or buffers.

Additives of this kind include, for example tartrate and citrate buffers, ethanol, complex formers (such as ethylenediamine-tetraacetic acid and the nontoxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in amounts of from 10 to 500 mg. per day, referred to a body weight of 75 kg. It is preferred to administer, 2 to 3 times a day, 1 to 2 tablets with an active material content of 5 to 200 mg. The tablets can also be retarded, in which case 1 to 2 tablets containing 10 to 500 mg. of active material are to be given once per day. The active material can also be administered by injection 1 to 8 times per day or by continuous infusion, in which case amounts of from 5 to 200 mg./day normally suffice.

As already mentioned, compounds of general formulae (VI) and (VII) are also new and are the subject of the present invention.

Apart from the compounds mentioned in the following Examples, compounds of general formula (VI) and (VII) according to the present invention also include the following compounds:

6-nitro-5-(2-furanylcarbonylamino)-indolin-2-one
6-nitro-5-(3-pyridazinylcarbonylamino)-3,3-dimethylindolin-2-one
6-nitro-5-[(6-methylpyrimidin-4-yl)-carbonylamino]-3,3-dimethylindolin-2-one
6-nitro-5-[(1,2,5-thiadiazol-3-yl)-carbonylamino]-3,3-dimethylindolin-2-one
6-nitro-5-[(1,3,4-thiadiazol-2-yl)-carbonylamino]-3,3-dimethylindolin-2-one
6-nitro-5-(2-furanylcarbonylamino)-3,3-diethylindolin-2-one
6-nitro-5-(4-pyridazinylcarbonylamino)-3-isopropylideneindolin-2-one
5-nitro-6-[(2-hydroxypyrimidin-5-yl)-carbonylamino]-3-methylindolin-2-one
5-nitro-6-[(3,6-dimethylpyridazin-4-yl)-carbonylamino]-3-methylindolin-2-one
5-nitro-6-[(1-methyl-2-oxopyrimidin-5-yl)-carbonylamino]-3-ethylindolin-2-one
5-nitro-6-[(1,2,5-oxadiazol-3-yl)-carbonylamino]-3-cyclopentylindolin-2-one
5-nitro-6-(3-pyridazinylcarbonylamino)-3-methyl-3-ethoxycarbonylindolin-2-one
5-nitro-6-(4-pyrimidinylcarbonylamino)-3-methyl-3-ethoxy-carbonylindolin-2-one
5-nitro-6-(2-pyrazinylcarbonylamino)-3-methyl-3-ethoxy-carbonylindolin-2-one
5-nitro-6-[(2-methylpyrimidin-5-yl)-carbonylamino]-3-methyl-3-ethoxycarbonylindolin-2-one
5-nitro-6-[(1-methyl-2-oxopyrimidin-5-yl)-carbonylamino]-3-methyl-3-ethoxycarbonylindolin-2-one
5-nitro-6-[(6-methylpyrimidin-4-yl)-carbonylamino]-3-methyl-3-ethoxycarbonylindoin-2-one
5-nitro-6-[(6-hydroxypyridazin-3-yl)-carbonylamino]-3-ethoxycarbonylindolin-2-one
5-nitro-6-[(3,6-dimethylpyridazin-4-yl)-carbonylamino]-3-ethoxycarbonylindolin-2-one
5-nitro-6-[(1,3,5-thiadiazol-2-yl)-carbonylamino]-3-ethoxycarbonylindolin-2-one
5-nitro-6-[(2-methylpyrimidin-5-yl)-carbonylamino]-3-methyl-3-acetylindolin-2-one.

New compounds of general formula (I) include, apart from the compounds mentioned in the Examples, also the following:

7,7-dimethyl-2-(3-pyridazinyl)-6,7-dihydro-3H,5H-pyrrolo[2,3-f]benzimidazol-6-one
7,7-dimethyl-2-(6-methylpyrimidin-4-yl)-6,7-dihydro-3H,5H-pyrrolo[2,3-f]benzimidazol-6-one
7,7-dimethyl-2-(3-pyrazolyl)-6,7-dihydro-3H,5H-pyrrolo[2,3-f]benzimidazol-6-one
7,7-dimethyl-2-(4-pyrazolyl)-6,7-dihydro-3H,5H-pyrrolo[2,3-f]benzimidazol-6-one
7,7-dimethyl-2-(2-thienylmethyl)-6,7-dihydro-3H,5H-pyrrolo[2,3-f]benzimidazol-6-one
7,7-dimethyl-2-(2,6-dihydroxyprimidin-4-yl)-6,7-dihydro-3H,5H-pyrrolo[2,3-f]benzimidazol-6-one
7,7-dimethyl-2-(4-oxazolyl)-6,7-dihydro-3H,5H-pyrrolo-[2,3-f]benzimidazol-6-one
7,7-dimethyl-2-(1,3,4-thiadiazol-2-yl)-6,7-dihydro-3H,5H-pyrrolo[2,3-f]benzimidazol-6-one
7,7-dimethyl-2-(1,2,3-thiadiazol-4-yl)-6,7-dihydro-3H,5H-pyrrolo[2,3-f]benzimidazol-6-one; m.p.>300° C., recrystallised from isopropanol
7,7-dimethyl-2-(1,2,3-thiadiazol-5-yl)-6,7-dihydro-3H,5H-pyrrolo[2,3-f]benzimidazol-6-one
7,7-dimethyl-2-(2-methylthio-1,3,4-oxadiazol-5-yl)-6,7-dihydro-3H,5H-pyrrolo[2,3-f]-benzimidazol-6-one
7,7-dimethyl-2-(4-carboxy-1,2,3-1H-triazol-5-yl)-6,7-dihydro-3H,5H-pyrrolo[2,3-f]benzimidazol-6-one
7,7-dimethyl-2-(4-methoxycarbonyl-1,2,3-1H-triazol-5-yl)-6,7-dihydro-3H,5H-pyrrolo[2,3-f]-benzimidazol-6-one
7,7-dimethyl-2-(4-aminocarbonyl-1,2,3-1H-triazol-5-yl)-6,7-dihydro-3H,5H-pyrrolo[2,3-f]-benzimidazol-6-one
7,7-dimethyl-2-(4-cyano-1,2,3-1H-triazol-5-yl)-6,7-dihydro-3H,5H-pyrrolo[2,3-f]benzimidazol-6-one
7,7-dimethyl-2-(5,6-dimethyl-1,2,4-triazin-3-yl)-6,7-dihydro-3H,5H-pyrrolo[2,3-f]benzimidazol-6-one
7,7-diethyl-2-(2-furanyl)-6,7-dihydro-3H,5H-pyrrolo-[2,3-f]benzimidazol-6-one
2'-(2-furanyl)-spiro[cyclopentan-1,7'-6',7'-dihydro-3'H,5'H-pyrrolo[2',3'-f]benzimidazol]-6'-one; m.p.>300° C., recrystallised from methyl ethyl ketone
2'-(4-pyridazinyl)-spiro[cyclopentan-1,7'-6',7'-dihydro-3'H,5'H-pyrrolo[2',3'-f]benzimidazol]-6'-one
7-methyl-2-(2-pyrrolyl)-6,7-dihydro-3H,5H-pyrrolo-[2,3-f]benzimidazol-6-one
7-methyl-2-(2-hydroxypyrimidin-5-yl)-6,7-dihydro-3H,5H-pyrrolo[2,3-f]benzimidazol-6-one
7-methyl-2-(3,6-dimethylpyridazin-4-yl)-6,7-dihydro-3H,5H-pyrrolo[2,3-f]benzimidazol-6-one
7-methyl-2-(2-oxopyran-5-yl)-6,7-dihydro-3H,5H-pyrrolo[2,3-f]benzimidazol-6-one
7-methyl-2-(2,6-dihydroxypyrimidin-4-yl)-6,7-dihydro-3H,5H-pyrrolo[2,3-f]benzimidazol-6-one
7-methyl-2-(2-oxazolyl)-6,7-dihydro-3H,5H-pyrrolo-[2,3-f]benzimidazol-6-one
7-methyl-2-(1,3,5-triazin-2-yl)-6,7-dihydro-3H,5H-pyrrolo[2,3-f]benzimidazol-6-one
7-ethyl-2-(4-imidazolyl)-6,7-dihydro-3H,5H-pyrrolo-[2,3-f]benzimidazol-6-one
7-ethyl-2-(1-methyl-2-oxopyrimidin-5-yl)-6,7-dihydro-3H,5H-pyrrolo[2,3-f]benzimidazol-6-one
7-ethyl-2-(2-imidazolyl)-6,7-dihydro-3H,5H-pyrrolo-[2,3-f]benzimidazol-6-one
7-ethyl-2-(3-methyl-1,2,4-triazin-5-yl)-6,7-dihydro-3H,5H-pyrrolo[2,3-f]benzimidazol-6-one
7-ethyl-2-(2-thiazolyl)-6,7-dihydro-3H,5H-pyrrolo-[2,3-f]benzimidazol-6-one
7-ethyl-2-(1,2,4-triazin-5-yl)-6,7-dihydro-3H,5H-pyrrolo-[2,3-f]benzimidazol-6-one
7-ethyl-2-(4-pyridazinyl)-6,7-dihydro-3H,5H-pyrrolo-[2,3-f]benzimidazol-6-one
7-isopropyl-2-(4-thiazolyl)-6,7-dihydro-3H,5H-pyrrolo-[2,3-f]benzimidazol-6-one
7-isopropyl-2-(1,2,4,5-tetrazin-3-yl)-6,7-dihydro-3H,5H-pyrrolo[2,3-f]benzimidazol-6-one
7-cyclopentyl-2-(5-thiazolyl)-6,7-dihydro-3H,5H-pyrrolo[2,3-f]benzimidazol-6-one 7-cyclopentyl-2-(1,2,5-oxadiazol-3-yl)-6,7-dihydro-3H,5H-pyrrolo[2,3-f]benzimidazol-6-one 7-isopropylidene-2-(4-pyridazinyl)-6,7-dihydro-3H,5H-pyrrolo[2,3-f]benzimidazol-6-one 7-isopropylidene-2-(1H-tetrazol-5-yl)-6,7-dihydro-3H,5H-pyrrolo[2,3-f]benzimidazol-6-one 2-(2-furanyl)-6,7-dihydro-3H,5H-pyrrolo[2,3-f]benzimidazol-6-one 7-methyl-7-ethoxycarbonyl-2-(3-pyridazinyl)-6,7-dihydro-3H,5H-pyrrolo[2,3-f]benzimidazol-6-one 7-methyl-7-ethoxycarbonyl-2-(4-pyrimidinyl)-6,7-dihydro-3H,5H-pyrrolo[2,3-f]benzimidazol-6-one 7-methyl-7-ethoxycarbonyl-2-(2-pyrazinyl)-6,7-dihydro-3H,5H-pyrrolo[2,3-f]benzimidazol-6-one 7-methyl-7-ethoxycarbonyl-2-(2-hydroxypyrimidin-5-yl)-6,7-dihydro-3H,5H-pyrrolo[2,3-f]benzimidazol-6-one 7-methyl-7-ethoxycarbonyl-2-(1-methyl-2-oxopyrimidin-5-yl)-6,7-dihydro-3H,5H-pyrrolo[2,3-f]benzimidazol-6-one 7-methyl-7-ethoxycarbonyl-2-(6-methylpyrimidin-4-yl)-6,7-dihydro-3H,5H-pyrrolo[2,3-f]benzimidazol-6-one 7-methyl-7-ethoxycarbonyl-2-(5-oxazolyl)-6,7-dihydro-3H,5H-pyrrolo[2,3-f]benzimidazol-6-one 7-methyl-7-ethoxycarbonyl-2-(2-thiazolyl)-6,7-dihydro-3H,5H-pyrrolo[2,3-f]benzimidazol-6-one 7-methyl-7-ethoxycarbonyl-2-(4-pyrazolyl)-6,7-dihydro-3H,5H-pyrrolo[2,3-f]benzimidazol-6-one 7-methyl-7-ethoxycarbonyl-2-(1,2,4-triazin-5-yl)-6,7-dihydro-3H,5H-pyrrolo[2,3-f]benzimidazol-6-one 7-methyl-7-ethoxycarbonyl-2-(5-methylpyrazol-5-yl)-6,7-dihydro-3H,5H-pyrrolo[2,3-f]benzimidazol-6-one 7-methyl-7-aminocarbonyl-2-(4-pyrimidinyl)-6,7-dihydro-3H,5H-pyrrolo[2,3-f]benzimidazol-6-one 7-methyl-7-aminocarbonyl-2-(5-oxazolyl)-6,7-dihydro-3H,5H-pyrrolo[2,3-f]benzimidazol-6-one 7-methyl-7-methylaminocarbonyl-2-(1-methyl-2-oxopyrimidin-5-yl)-6,7-dihydro-3H,5H-pyrrolo[2,3-f]benzimidazol-6-one 7-methyl-7-methylaminocarbonyl-2-(1,3,4-triazin-5-yl)-6,7-dihydro-3H,5H-pyrrolo[2,3-f]benzimidazol-6-one 7-methyl-7-dimethylaminocarbonyl-2-(6-methylpyrimidin-4-yl)-6,7-dihydro-3H,5H-pyrrolo[2,3-f]benzimidazol-6-one 7-methyl-7-dimethylaminocarbonyl-2-(5-methylpyrazol-3-yl)-6,7-dihydro-3H,5H-pyrrolo[2,3-f]benzimidazol-6-one 7-methyl-7-cyano-2-(2-pyrazinyl)-6,7-dihydro-3H,5H-pyrrolo[2,3-f]benzimidazol-6-one 7-methyl-7-cyano-2-(2-thiazolyl)-6,7-dihydro-3H,5H-pyrrolo[2,3-f]benzimidazol-6-one 7-methyl-7-hydrazinocarbonyl-2-(2-methylpyrimidin-5-yl)-6,7-dihydro-3H,5H-pyrrolo[2,3-f]benzimidazol-6-one 7-methyl-7-hydrazinocarbonyl-2-(4-pyrazolyl)-6,7-dihydro-3H,5H-pyrrolo[2,3-f]benzimidazol-6-one 7-methyl-7-acetyl-2-(2-hydroxypyrimidin-5-yl)-6,7-dihydro-3H,5H-pyrrolo[2,3-f]benzimidazol-6-one 7-methyl-7-acetyl-2-(1,3,5-triazin-2-yl)-6,7-dihydro-3H,5H-pyrrolo[2,3-f]benzimidazol-6-one 7-ethoxycarbonyl-2-(6-hydroxypyridazin-3-yl)-6,7-dihydro-3H,5H-pyrrolo[2,3-f]benzimidazol-6-one 7-ethoxycarbonyl-2-(3,6-dimethylpyridazin-4-yl)-6,7-dihydro-3H,5H-pyrrolo[2,3-f]benzimidazol-6-one 7-ethoxycarbonyl-2-(1,2,4-triazol-3-yl)-6,7-dihydro-3H,5H-pyrrolo[2,3-f]benzimidazol-6-one 7-ethoxycarbonyl-2-(3-pyrazolyl)-6,7-dihydro-3H,5H-pyrrolo[2,3-f]benzimidazol-6-one 7-ethoxycarbonyl-2-(1,2,5-thiadiazol-3-yl)-6,7-dihydro-3H,5H-pyrrolo[2,3-f]benzimidazol-6-one 7-ethoxycarbonyl-2-(2-oxopyran-5-yl)-6,7-dihydro-3H,5H-pyrrolo[2,3-f]benzimidazol-6-one 7-ethoxycarbonyl-2-(1,3,4-thiadiazol-2-yl)-6,7-dihydro-3H,5H-pyrrolo[2,3-f]benzimidazol-6-one 7-aminocarbonyl-2-(3,6-dimethylpyridazin-4-yl)-6,7-dihydro-3H,5H-pyrrolo benzimidazol-6-ones 7-methylaminocarbonyl-2-(1,2,5-thiadiazol-3-yl)-6,7-dihydro-3H,5H-pyrrolo benzimidazol-6-one 7-dimethylaminocarbonyl-2-(2-oxopyran-5-yl)-6,7-dihydro-3H,5H-pyrrolo benzimidazol-6-one 7-cyano-2-(1,2,4-triazol-3-yl)-6,7-dihydro-3H, 5H-pyrrolo-benzimidazol-6-one 7-hydrazinocarbonyl-2-(3-pyrazolyl)-6,7-dihydro-3H, 5H-pyrrolo-benzimidazol-6-one 7-acetyl-2-(2-imidazolyl)-6,7-dihydro-3H,5H-pyrrolo[2,3-f]benzimidazol-6-one.

The following Examples are given for the purpose of illustrating the present invention:

EXAMPLE 1

7,7-Dimethyl-2-(2-furanyl)-6,7-dihydro-3H,5H-pyrrolo[2,3-f]benzimidazol-6-one.

(a) 6.5 g. (50 mmol) furan-2-carboxylic acid chloride are added dropwise, with ice cooling, to a solution of 5.5 g. (25 mmol) 6-amino-5-nitro-3,3-dimethylindolin-2-one in 50 ml. pyridine and then stirred at 25° C. The crystalline slurry obtained is poured into about 300 ml. water, filtered off with suction, washed with water and dried. The crude product is further used without purification. There are obtained 10.2 g. 6-furanylcarbonylamino-5-nitro-3,3-dimethylindolin-2-one; m.p. 229°-235° C.

(b) 1.0 g. Palladium on charcoal (10%) are added to 10.0 g. (31.7 mmol) 6-(2-furanylcarbonylamino)-5-nitro-3,3-dimethylindolin-2-one in 250 ml. ethanol. This suspension is hydrogenated at ambient temperature and normal pressure. After completion of the take-up of hydrogen, the solution is separated from the catalyst and evaporated to dryness. The crude product is further used without purification. There are obtained 9.5 g. 6-furanoylamino-5-amino-3,3-dimethylindolin-2-one; m.p. 215°-224° C.

(c) 5.7 g. (20 mmol) 6-furanoylamino-5-amino-3,3-dimethylindolin-2-one are heated for 1 hour at 80° C. in 200 ml. ethanol and 40 ml. concentrated hydrochloric acid. The solution is evaporated to dryness, rendered alkaline with 2N aqueous ammonia solution and extracted with methylene chloride. The organic phase is evaporated and the residue purified over silica gel (elution agent: methylene chloride/ammonia-saturated methanol 20:1 v/v). There is obtained 1.8 g. (33.3% of theory) of the desired product; m.p. 311°-316° C. after recrystallisation from ethyl acetate.

EXAMPLE 2

7,7-Dimethyl-2-(2-thienyl)-6,7-dihydro-3H,5H-pyrrolo[2,3-f]benzimidazol-6-one.

A solution of 3.8 g. (20 mmol) 5,6-diamino-3,3-dimethylindolin-2-one, 2.25 g. (20 mmol) thiophene-2-aldehyde and 4 ml. glacial acetic acid in 40 ml. ethanol is heated under reflux for 1 hour and then further boiled for 1 hour, while passing through air. The reaction mixture is then distilled to dryness and the residue stirred up with ethyl acetate and filtered off with suction. The crystallisate obtained is recrystallised from acetone. Yield: 1.7 g. (30% of theory); m.p. 332°–336° C.

EXAMPLE 3

7,7-Dimethyl-2-(2-pyrrolyl)-6,7-dihydro-3H,5H-pyrrolo[2,3-f]benzimidazol-6-one

Analogously to Example 2, from 3.8 g. (20 mmol) 5,6-diamino-3,3-dimethylindolin-2-one, 1.9 g. (20 mmol) pyrrole-2-aldehyde and 0.4 g. (2 mmol) p-toluene-sulphonic acid, after acidification and evaporation of the reaction mixture, there is obtained the crude product of the title compound. For purification, the residue is worked up with water and the filtrate is neutralised with 2N aqueous ammonia solution and filtered off with suction. The residue is recrystallised from isopropanol with the addition of ethanolic hydrochloric acid. The yield is 1.2 g. (20% of theory); m.p. of the hydrochloride > 300° C.

EXAMPLE 4

7,7-Dimethyl-2-(2-pyrazinyl)-6,7-dihydro-3H,5H-pyrrolo[2,3-f]benzimidazol-6-one.

(a) 5.1 g. (26 mmol) 5,6-diamino-3,3-dimethylindolin-2-one are dissolved in 100 ml. methylene chloride and mixed with 5.5 g. (39 mmol) pyrazine-2-carboxylic acid chloride and 3.9 g. (39 mmol) triethylamine. After 1 hour at 25° C., the solvent is distilled off and the residue is worked up with water and filtered off with suction. The residue of mono- and diamide is recrystallised from ethyl acetate/methanol. Yield: 5.6 g.; m.p. 269°–272° C.

(b) 5.6 g. of the mono- and diamide are stirred for 18 hours at 90° C. with 85 ml. ethanol and 85 ml. concentrated hydrochloric acid. Subsequently, the reaction mixture is evaporated, neutralised with 2N aqueous ammonia solution and filtered off with suction. The residue is purified over silica gel (elution agent: methylene chloride/methanol 19:1 v/v) and recrystallised from ethyl acetate/methanol. Yield: 0.85 g. (16% of theory); m.p. > 300° C.

EXAMPLE 5

7,7-Dimethyl-2-(4-thiazolyl)-6,7-dihydro-3H,5H-pyrrolo[2,3-f]benzimidazol-6-one

Analogously to Example 4, starting from 3.8 g. (20 mmol) 5,6-diamino-3,3-dimethylindolin-2-one and 4.4 g. (30 mmol) thiazole-4-carboxylic acid chloride, there is obtained the title compound. Yield: 1.9 g. (33% of theory); m.p. 280° C., after crystallisation from methanol.

EXAMPLE 6

7,7-Dimethyl-2-(4-pyridazinyl)-6,7-dihydro-3H,5H-pyrrolo[2,3-f]benzimidazol-6-one (a) 5.4 g. (40 mmol) 1-hydroxy-1H-benzotriazole are placed, together with 5 g. calcium sulphate and 4.3 g. (35 mmol) pyridazine-4-carboxylic acid, in anhydrous dimethylformamide. 8.3 g. (40 mmol) N,N-dicyclohexyl carbodiimide in a little dimethylformamide are added dropwise thereto at 0° C. After complete formation of the activated ester, 5.7 g. (30 mmol) 5,6-diamino-3,3-dimethylindolin-2-one are added thereto and the reaction mixture is then stirred for 30 minutes. The dimethylformamide is distilled off in a high vacuum, the residue is worked up with water and the crude product of monoamide and dicyclohexylurea is filtered off with suction and further used without purification. Yield: 20 g.

(b) The residue obtained according to (a) is mixed with 200 ml. ethanol and 40 ml. concentrated hydrochloric acid and heated under reflux for 2 hours. After cooling, the dicyclohexylurea is filtered off with suction and the ethanolic solution evaporated in a vacuum. The residue is suspended in water, rendered alkaline with 2N aqueous ammonia solution and the title compound is filtered off with suction and recrystallised, with cooling, from ethyl acetate. Yield: 1.0 g. (12% of theory); m.p. > 360° C.

EXAMPLE 7

7-Methyl-2-(4-pyridazinyl)-6,7-dihydro-3H,5H-pyrrolo-[2,3-f]benzimidazol-6-one

Analogously to Example 6, starting from 6.0 g. (24 mmol) 5,6-diamino-3-methylindolin-2-one dihydrochloride and 3.6 g. (28.8 mmol) pyridazine-4-carboxylic acid, there is obtained the title compound. Furification takes place by column chromatography on silica gel (elution agent: methylene chloride/methanol 9:1 v/v). Yield: 0.15 g. (2.4% of theory): m.p. > 340° C.

EXAMPLE 8

7,7-Dimethyl-2-(5-pyrimidinyl)-6,7-dihydro-3H,5H-pyrrolo[2,3-f]benzimidazol-6-one Analogously to Example 6, from 0.164 g. (1.32 mmol) pyrimidine-5-carboxylic acid and 0.191 g. (1 mmol) 5,6-diamino-3,3-dimethylindolin-2-one is obtained, after cyclisation of the crude product with glacial acetic acid, the title compound. Yield: 70 mg. (25% of theory); m.p. 310°–312° C. after recrystallisation from dioxan.

EXAMPLE 9

7,7-Dimethyl-2-(4-pyrimidinyl)-6,7-dihydro-3H,5H-pyrrolo[2,3-f]benzimidazol-6-one Analogously to Example 2, from 60 mg. (0.55 mmol) pyrimidine-4-aldehyde and 0.103 g. (0.54 mmol) 5,6-diamino-3,3-dimethylindolin-2-one, after column chromatography on silica gel (elution agent: methylene chloride/methanol 9:1 v/v), there is obtained the title compound. Yield: 10 mg. (6.6% of theory); m.p. > 300° C.

EXAMPLE 10

7,7-Dimethyl-2-(2-methylpyrimidin-5-yl)-6,7-dihydro-3H,5H-pyrrolo[2,3-f]benzimidazol-6-one Analogously to Example 6, starting from 5.7 g. (30 mmol) 5,6-diamino-3,3-dimethylindolin-2-one and 4.8 g.

(35 mmol) 2-methylpyrimidine-5-carboxylic acid, there is obtained the monoamide. Yield: 3.6 g. (39% of theory); m.p. 166°–170° C. after recrystallisation from water.

The crude product is subsequently cyclised with glacial acetic acid to give the title compound. Yield: 2.3 g. (68.5% of theory); m.p. >350° C.

EXAMPLE 11

7,7-Dimethyl-2-(4-imidazolyl)-6,7-dihydro-3H,5H-pyrrolo[2,3-f]benzimidazol-6-one Analogously to Example 4, starting from 2.7 g. (14.1 mmol) 5,6-diamino-3,3-dimethylindolin-2-one and 2.8 g. (21.5 mmol) imidazole-4-carboxylic acid chloride, there is obtained the title compound. Yield: 0.17 g. (4.5% of theory); m.p. 270° C., after recrystallisation from methanol.

EXAMPLE 12

7,7-Dimethyl-2-(6-hydroxypridazin-3-yl)-6,7-dihydro-3H,5H-pyrrolo[2,3-f]benzimidazol-6-one Analogously to Example 8, starting from 4.9 g. (35 mmol) 6-hydroxypyridazine-3-carboxylic acid and 5.7 g. (30 mmol) 5,6-diamino-3,3-dimethylindolin-2-one, there is obtained the title compound. Yield: 2.8 g. (32% of theory); m.p. >350° C., recrystallised from ethanol.

EXAMPLE 13

7,7-Dimethyl-2-(1,2,4-1H-triazol-3-yl)-6,7-dihydro-3H,5H-pyrrolo[2,3-f]benzimidazol-6-one Analogously to Example 2, starting from 0.38 g. (2 mmol) 5,6-diamino-3,3-dimethylindolin-2-one and 0.195 g. (2 mmol) 1,2,4-triazole-3-aldehyde, there is obtained the title compound. Yield: 0.15 g. (28% of theory); m.p. >350° C.

EXAMPLE 14

7,7-Dimethyl-2-(2-methyloxazol-4-yl)-6,7-dihydro-3H,5H-pyrrolo[2,3-f]benzimidazol-6-one Analogously to Example 10, starting from 764 mg. (4 mmol) 5,6-diamino-3,3-dimethylindolin-2-one and 672 mg. (5.32 mmol) 2-methyloxazole-4-carboxylic acid, there is obtained the title compound after purification on silica gel (elution agent: methylene chloride/methanol 8:2 v/v). Yield: 0.3 g. (26.6% of theory); m.p. 315°–318° C.

EXAMPLE 15

7,7-Dimethyl-2-(5-methylpyrazol-3-yl)-6,7-dihydro-3H,5H-pyrrolo[2,3-f]benzimidazol-6-one Analogously to Example 2, starting from 0.57 g. (3 mmol) 5,6-diamino-3,3-dimethylindolin-2-one and 0.33 g. (3 mmol) 5-methylpyrazole-3-aldehyde, there is obtained the crude product after rendering the reaction mixture alkaline with concentrated aqueous ammonia solution. The residue is purified over silica gel (elution agent: methylene chloride/ammonia-saturated methanol 10:3 v/v). Yield: 0.22 g. (26% of theory); m.p. 245°–250° C., crystallised from water.

EXAMPLE 16

7-Methyl-7-ethoxycarbonyl-2-(2-pyrazinyl)-6,7-dihydro-3H,5H-pyrrolo[2,3-f]benzimidazol-6-one (a) 5.0 g. (18.5 mmol) 3-methyl-3-ethoxycarbonyl-6-aminoindolin-2-one hydrochloride are suspended in 60 ml. methylene chloride and mixed with 12.5 ml. (90.4 mmol) triethylamine. 6.4 g. (45.2 mmol) pyrazine-2-carboxylic acid chloride are then added portionwise, while cooling with ice, and the reaction mixture is further stirred for 3 hours. The reaction mixture is evaporated, worked up with water, filtered off with suction and purified by column chromatography elution agent: methylene chloride/methanol 99:1 v/v). There are obtained 4.0 g. (65% of theory) of the title compound; m.p.

(b) 3.4 g. (10 mmol) 3-methyl-3-ethoxycarbonyl-6-(2-pyrazinoylamino)-indolin-2-one are dissolved in 20 ml. concentrated sulphuric acid and mixed dropwise at 0° to 5° C. with a solution of 1.1 g. (11 mmol) potassium nitrite in concentrated sulphuric acid. After 3 hours, the reaction mixture is poured on to ice, filtered off with suction and the residue is suspended in water, neutralised with aqueous ammonia solution, filtered off with suction and recrystallised from ethanol. There are obtained 3.2 g. (83% of theory) 3-methyl-3-ethoxycarbonyl-5-nitro-6-(2-pyrazinolylamino)indolin-2-one: m.p.

(c) 3.2 g. (8.3 mmol) 3-methyl-3-ethoxycarbonyl-5-nitro-6-(2-pyrazinoylamino)-indolin-2-one in 100 ml. ethanol are hydrogenated in 100 ml. ethanol in the presence of 0.5 g. 10% palladium on charcoal. After completion of the take up of hydrogen, the solution is filtered off from the catalyst, the ethanol is evaporated off and the residue is stirred for 1 hour in glacial acetic acid at 60° C.

EXAMPLE 17

7,7-Dimethyl-2-(1,2,5-thiadiazol-3-yl)-6,7-dihydro-3H,5H-pyrrolo[2,3-f]benzimidazol-6-one 2.0 g. (15.3 mmol) 1,2,5-thiadiazole-3-carboxylic acid and 2.6 g. (13.6 mmol) 5,6-diamino-3,3-dimethyl-indolin-2-one are heated in 40 ml. polyphosphoric acid under an atmosphere of nitrogen for 2 hours at 160° C. The warm solution is poured on to ice water, worked up and the crystals obtained are filtered off with suction.

The residue is again suspended in water, neutralised with an aqueous solution of ammonia, filtered off with suction and recrystallised from methanol with the addition of charcoal. Yield: 2.6 g. (66% of theory); m.p. >300° C.

PHARMACEUTICAL ACTIVITY

The following experiment demonstrates the pharmaceutical activity of compound (I) of the invention:

Male Sprague-Dawley rats weighing between 350 and 450 g were narcotized by intraperitoneal injection of a barbiturate and fitted with instrumentation for the examinations as follows:

A pressure measuring catheter (Millar Mikrotip TM-/diameter 0.5 mm) was inserted through the arteria carotis dextra into the left ventricle. The pressure inside the left ventricle was continually registered through this catheter. The signal from this mikrotip was elecronically differentiated and $(dp/dt)_{60}$—the slope of the pressure-time curve at a pressure of 60 mm Hg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on a electrically heated and thermostated operating table.

The test substances were always introduced by intravenous injection, with an injection volume, per injection, of 1 ml/kg body weight. In intervals of 10 min. each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $\Delta$ (dp/dt)$_{60}$ were calculated. In addition, as criteria for the effectiveness of the substances, the maximum effect obtained maximal increase of (dp/dt)$_6$ and its corresponding dose were determined. Table (I) below shows the equipotent doses (DE$_{1.5}$=the dose in mg/kg that leads to an increase of (dp/dt)$_{60}$ of 1.5 mHg/sec) and the maximal effectiveness (W$_{max}$=the maximal increase of (dp/dt)$_{60}$.

TABLE (I)

| Substance | DE$_{1.5}$ mHg/sec [mg/kg i.v.] | W$_{max}$ [mHg/sec] | [mg/kg i.v.] |
|---|---|---|---|
| Ex. 1 | 0.07 | 2,9 | 3,0 |
| Ex. 2 | 0.12 | 2,1 | 0,3 |
| Ex. 3 | 0.45 | 2,6 | 10,0 |
| Ex. 4 | 0,10 | 2,6 | 10,0 |
| Ex. 5 | 0.14 | 2,0 | 0,3 |
| Ex. 6 | 0,04 | 2,4 | 0,3 |
| Ex. 8 | 0,05 | 3.1 | 3,0 |
| Ref. 1 | 1.17 | 3.5 | 10 |
| Ref. 2 | >>3.0 | 0.6 | 3.0 |

The corresponding dose is shown in brackets.

The values show, that the substances of Example 6,8 and 1 are more potent than the substances, used as standards (Ref. 1 and Ref. 2).

Ref. 1: 3-Amino-6-methyl-5-phenyl-2-(1H)-pyridinone-methane-sulfonate (from British Patent Application GB No. 2,070,606).

Ref. 2: 3,4-Dihydro-6-[4-[3,4-dimethoxybenzoyl)-1-piperazinyl]-2 (1H)-quinolinone (from U.S. Pat. No. 4,415,572).

It will be understood that the specification and examples are illustrative but not limitative of the present invention and that other embodiments within the spirit and scope of the invention will suggest themselves to those skilled in the art.

What is claimed is:

1. A pyrrolobenzimidazole or tautomer thereof, of the formula:

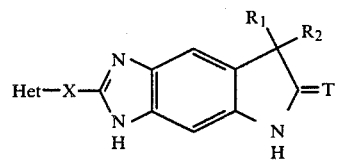

(I)

wherein
R$_1$ is hydrogen, C$_1$–C$_6$ alkyl, C$_2$—C$_6$ alkenyl or C$_3$–C$_7$cycloalkyl;
R$_2$ is hydrogen, cyano, C$_1$–C$_6$ alkyl, C$_2$–C$_6$ alkenyl, or a carbonyl group substituted by hydroxyl, C$_1$–C$_6$ alkyl, C$_1$–C$_6$ alkoxy, amino, C$_1$–C$_6$ alkylamino, C$_2$–C$_{12}$ dialkylamino or hydrazino, or R$_2$ and R$_1$ together with the carbon to which they are attached form a C$_3$-C$_8$ spirocycloalkyl ring, or R$_1$ and R$_2$ together form C$_3$–C$_7$ alkylidene or C$_3$–C$_7$ cycloalkylidene,
X is a valency bond, C$_1$–C$_4$ alkylene or vinylene and T is oxygen or sulphur;
and Het is furanyl, thienyl, pyrrolyl, pyrazolyl, imidazolyl, oxazolyl, thiazolyl, triazolyl, oxadiazolyl, thiadiazolyl, pyrazinyl, pyrimidinyl or pyridazinyl wherein the heterocyclic five- and six-membered rings are unsubstituted or substituted by one or more C$_1$–C$_6$ alkyl, C$_1$–C$_6$ alkoxy, C$_1$–C$_6$ alkylthio, hydroxyl, oxo, nitro, amino, halo, carboxyl, C$_2$–C$_7$ alkoxycarbonyl, aminocarbonyl or cyano groups; or a physiologically acceptable salt thereof with an inorganic or organic acid.

2. The pyrrolobenzimidazole of claim 1, wherein R$_1$ is hydrogen, methyl, ethyl, cyclopentyl or cyclohexyl, and R$_2$ is hydrogen, methyl, ethyl, isopropyl, 3-pentyl, allyl, cyano, acetyl, propionyl, methoxycarbonyl, ethoxycarbonyl, aminocarbonyl, methylaminocarbonyl, dimethylaminocarbonyl or hydrazinocarbonyl or R$_1$ and R$_2$, together with the carbon atom to which they are attached, represent a sipirocyclopropyl, spirocyclobutyl, spirocyclopentyl or spirocyclohexyl ring or R$_1$ and R$_2$ together represent isopropylidene, X is a valency bond, or methylene or vinylene, T is oxygen and Het is pyrrolyl, furanyl, pyrazolyl, imidazolyl, thiazolyl, oxazolyl, triazolyl, thiadiazolyl, oxadiazolyl, pyrazinyl, pyrimidinyl thienyl or pyridazinyl, wherein the heterocyclic five- or six-membered rings are unsubstituted or substituted one or more times by oxo, hydroxyl, methyl, methoxy, methylthio, carboxyl, methoxycarbonyl, ethoxycarbonyl, aminocarbonyl, amino, nitro, halo or cyano.

3. The pyrrolobenzimidazole of claim 1 wherein R$_1$ is a hydrogen, methyl or ethyl, R$_2$ is a methyl, ethyl or ethoxycarbonyl or R$_1$ and R$_2$, together with the carbon atom to which they are attached, form a spirocyclopentane ring, X is a valency bond or methylene, T is oxygen and Het is furanyl, thienyl, pyrrolyl, thiazolyl, imidazolyl, triazolyl, oxazolyl, oxadiazolyl, pyrazolyl, thiadiazolyl, pyrazinyl, pyridazinyl, or pyrimidinyl, wherein the heterocyclic rings are unsubstituted or substituted one or more times by hydroxyl, methyl or carboxyl.

4. The pyrrolobenzimidazole of claim 1, wherein R$_1$ and R$_2$ are methyl or ethyl, X is a valency bond, T is oxygen and Het is furanyl, thienyl, pyrrolyl, pyrazinyl, thiazolyl, thiadiazolyl, pyridazinyl or pyrimidinyl.

5. The pyrrolobenzimidazole of claim 1 wherein R$_1$ and R$_2$ are the same and are methyl or ethyl.

6. The pyrrolobenzimidazole of claim 1 wherein R$_1$ and R$_2$ form isopropylidene.

7. The pyrrolobenzimidazole of claim 1 wherein R$_1$ and R$_2$ form a C$_3$-C$_8$ spirocycloalkyl ring.

8. The pyrrolobenzimidazole of claim 1 wherein R$_1$ and R$_2$ form a C$_3$-C$_6$ spirocyloalkyl ring.

9. The pyrrolobenzimidazol of claim 1 designated 7,7-dimethyl-2-(2-furanyl)-6,7-dihydro-3H, 5H-pyrrolo benzimidazol-6-one.

10. The pyrrolobenzimidazole of claim 1 designated 7,7-dimethyl-2-(4-pyridazinyl)-6,7-dihydro-3H, 5H-pyrrolo benzimidazol-6-one.

11. The pyrrolobenzimidazol of claim 1 designated 7,7-dimethyl-2-(5-pyrimidinyl)-6,7-dihydro-3H,5H-pyrrolo benzimidazol-6-one.

12. The pyrrolobenzimidazole of claim 1 wherein Het is furanyl, thienyl, pyrrolyl, thiazolyl, triazolyl, oxazolyl, pyrazolyl, thiadiazolyl, pyrazinyl, pyridazinyl, or pyrimidinyl, wherein the heterocyclic rings are unsubstituted or are substituted one or more times by hydroxyl, methyl, or carboxyl.

13. The pyrrolobenzimidazole of claim 1 Het is furanyl, thienyl, pyrrolyl, thiazolyl, triazoly, thiadiazolyl, pyrazinyl, pyridazinyl, or pyrimidinyl, wherein the heterocyclic rings are unsubstituted or are substituted one or more times by hydroxyl, methyl, or carboxyl.

14. The pyrrolobenzimidazole of claim 1 wherein Het is furanyl, thienyl, pyrrolyl, thiazolyl, pyrazinyl, pyridazinyl or pyrimidinyl wherein the heterocyclic rings are unsubstituted or are substituted one or more times by hydroxyl, methyl, or carboxyl.

15. A pharmaceutical composition containing an effective amount of at least one pyrrolobenzimidazole of claim 1 for the prophylaxis or treatment of heart or circulatory diseases which respond to a change of blood pressure, an increase in cardiac output and/or a change in microcirculation.

16. The pharmaceutical composition of claim 12 wherein said compound is 7,7-dimethyl-2-(2-furanyl)-6,7-dihydro-3H, 5H-pyrrolo benzimidazol-6-one or 7,7-dimethyl-2-(4-pyridazinyl)-6,7-dihydro-3H, 5H-pyrrolo benzimidazol-6-one or 7,7-dimethyl-2-(5-pyrimidinyl)-6,7-dihydro-3H, 5H-pyrrolo benzimidazol-6-one.

17. A method of treating heart or circulatory diseases which respond to a change of blood pressure, an increase in cardiac output and/or a change in microcirculation comprising administering an effective amount for treating said heart or circulatory diseases, of the pyrrobenzimidazole of claim 1.

18. The method of claim 17, wherein 10 to 500 mg per 75 kg body weight, are administered per day.

* * * * *

UNITED STATES PATENT AND TRADEMARK OFFICE
CERTIFICATE OF CORRECTION

PATENT NO. : 4,695,567

DATED : September 22, 1987

INVENTOR(S) : Alfred Mertens

It is certified that error appears in the above-identified patent and that said Letters Patent is hereby corrected as shown below:

Column 14, lines 8, 10, 12, 14 and 16:     after "dihydro-3H,5H-pyrrolo" insert -- [2,3-f] --.

Column 14, line 8:     change "benzimidazole-6-ones" to -- benzimidazole-6-one --.

Column 18, line 6:     after "chromatography" insert -- ( --.

Column 18, line 21:     change "(2-pyrazinolylamino)" to -- (2-pyrazinoylamino) --.

Column 19, line 17:     change "$(dp/dt)_6$" to -- $(dp/dt)_{60}$ --.

Column 19, line 43:     change "3,4-Dihydro-6-[4-[3,4-dimethoxybenzoyl]" to -- 3,4-Dihydro-6-[4-(3,4-dimethoxybenzoyl) -- .

Column 21, line 8 (new claim 13):     change "triazoly" to -- triazolyl --.

Column 22, line 4 (new claim 16):     after "claim" delete "12" and insert -- 15 --.

UNITED STATES PATENT AND TRADEMARK OFFICE
CERTIFICATE OF CORRECTION

PATENT NO. : 4,695,567

DATED : September 22, 1987

INVENTOR(S) : Alfred Mertens

It is certified that error appears in the above-identified patent and that said Letters Patent is hereby corrected as shown below:

Column 22, lines 15-16: change "pyrrobenzimidazole" to
-- pyrrolobenzimidazole --.

Signed and Sealed this

Twenty-fifth Day of October, 1988

Attest:

DONALD J. QUIGG

Attesting Officer

Commissioner of Patents and Trademarks